US012361669B2

(12) United States Patent
Zhang et al.

(10) Patent No.: US 12,361,669 B2
(45) Date of Patent: Jul. 15, 2025

(54) PERSONALIZED TARGET SELECTION METHOD FOR NON-INVASIVE NEUROMODULATION TECHNOLOGY

(71) Applicant: THE AFFILIATED BRAIN HOSPITAL OF NANJING MEDICAL UNIVERSITY, Nanjing (CN)

(72) Inventors: Xizhe Zhang, Nanjing (CN); Fei Wang, Nanjing (CN)

(73) Assignee: THE AFFILIATED BRAIN HOSPITAL OF NANJING MEDICAL UNIVERSITY, Nanjing (CN)

( * ) Notice: Subject to any disclaimer, the term of this patent is extended or adjusted under 35 U.S.C. 154(b) by 0 days.

(21) Appl. No.: 19/026,895

(22) Filed: Jan. 17, 2025

(65) Prior Publication Data
US 2025/0157175 A1    May 15, 2025

Related U.S. Application Data

(63) Continuation of application No. PCT/CN2024/079519, filed on Mar. 1, 2024.

(30) Foreign Application Priority Data

Mar. 21, 2023   (CN) .......................... 202310279372.1

(51) Int. Cl.
G06K 9/00       (2022.01)
A61B 5/00       (2006.01)
(Continued)

(52) U.S. Cl.
CPC ............ *G06V 10/25* (2022.01); *A61B 5/0042* (2013.01); *A61B 5/055* (2013.01); *G06T 7/0014* (2013.01);
(Continued)

(58) Field of Classification Search
CPC ....... A61B 5/055; A61B 5/0042; A61B 5/316; A61B 34/10; A61B 5/4064;
(Continued)

(56) References Cited

U.S. PATENT DOCUMENTS 6,266,453 B1 * 7/2001 Hibbard .................... G06T 3/02
382/294
2011/0245625 A1 * 10/2011 Trovato ............. A61B 17/3421
600/300

(Continued)

FOREIGN PATENT DOCUMENTS

CN    111407276 A    7/2020
CN    113367680 A    9/2021
(Continued)

OTHER PUBLICATIONS

Cordes et al. "Frequencies Contributing to Functional Connectivity in the Cerebral Cortex in "Resing-state" Data" AJNR Am J Neuroradiol 22: 1326-1333, Aug. 2001 (Year: 2001).*
(Continued)

Primary Examiner — Alex Kok S Liew
(74) Attorney, Agent, or Firm — Bayramoglu Law Offices LLC

(57) ABSTRACT

The provided is a personalized target selection method for a non-invasive neuromodulation technology, including: preprocessing functional magnetic resonance imaging (fMRI) data from MRI scan data of a current patient to acquire fMRI brain image feature data; inputting the fMRI brain image feature data into a pre-trained inter-subtype classification model to acquire a subtype label of the current patient and all feature voxels of the subtype label; preprocessing T1-weighted MRI data of structural magnetic resonance imaging (sMRI) data from the MRI scan data of the current patient to acquire a skull outline and a transformation matrix between the sMRI and fMRI data; performing coordinate
(Continued)

transformation on the feature voxels, calculating a distance between each voxel on the skull outline and each feature voxel, marking response feature voxels, and counting a number of response feature voxels; and sorting the number of response feature voxels.

20 Claims, 3 Drawing Sheets

(51) Int. Cl.
| | |
|---|---|
| *A61B 5/055* | (2006.01) |
| *G06T 7/00* | (2017.01) |
| *G06T 7/73* | (2017.01) |
| *G06V 10/25* | (2022.01) |
| *G06V 10/26* | (2022.01) |
| *G06V 10/32* | (2022.01) |
| *G06V 10/764* | (2022.01) |
| *G06V 10/774* | (2022.01) |
| *G06V 20/70* | (2022.01) |

(52) U.S. Cl.
CPC ............... *G06T 7/73* (2017.01); *G06V 10/26* (2022.01); *G06V 10/32* (2022.01); *G06V 10/764* (2022.01); *G06V 10/774* (2022.01); *G06V 20/70* (2022.01); *G06T 2207/10088* (2013.01); *G06T 2207/20081* (2013.01); *G06T 2207/30016* (2013.01); *G06T 2207/30242* (2013.01); *G06V 2201/031* (2022.01)

(58) Field of Classification Search
CPC ... A61B 2034/105; A61B 5/369; A61B 5/291; A61B 2034/107; A61B 5/0035; G06T 2207/10088; G06T 7/11; G06T 2207/30016; G06T 2207/20081; G06T 2207/20084; G06T 7/0012; G06T 2207/10081; G06T 2207/30096; G06T 7/10; G06T 2210/41; G06T 17/00; G06T 2207/10072; G06T 2207/10104; G06T 7/33; G06T 7/37; G06T 2207/30004; G06T 7/174; G06T 7/38; G06T 19/20; G06T 2207/20008; G06T 7/0014
See application file for complete search history.

(56) References Cited

U.S. PATENT DOCUMENTS

| | | | |
|---|---|---|---|
| 2015/0272469 A1* | 10/2015 | Fox | A61B 5/055 600/410 |
| 2021/0106830 A1* | 4/2021 | Provenza | A61B 5/37 |
| 2021/0170180 A1 | 6/2021 | Dosenbach et al. | |

FOREIGN PATENT DOCUMENTS

| | | |
|---|---|---|
| CN | 115424067 A | 12/2022 |
| CN | 116433967 A | 7/2023 |

OTHER PUBLICATIONS

Xia Qingling, et al., The application and prospect of combined functional magnetic resonance imaging and transcranial magnetic stimulation on the modulation of brain functional network, Chin J Magn Reson Imaging, 2022, pp. 117-120, 129, vol. 13 No. 8.

Matthew S. Sherwood, et al., Combining Real-Time fMRI Neuro feedback Training of the DLPFC with N-Back Practice Results in Neuro plastic Effects Confined tot he Neuro feed back Target Region, Frontiers in Behavioral Neuroscience, 2016, pp. 1-9, vol. 10 No. 138.

* cited by examiner

Subtype 1

| Voxel features | Accuracy | F1 | Precession | Recall |
|---|---|---|---|---|
| Top-50 voxels | 0.762 | 0.614 | 0.629 | 0.606 |
| All-brain-region voxels | 0.714 | 0.630 | 0.623 | 0.657 |

Subtype 2

| Voxel features | Accuracy | F1 | Precession | Recall |
|---|---|---|---|---|
| Top-50 voxels | 0.697 | 0.673 | 0.698 | 0.671 |
| All-brain-region voxels | 0.727 | 0.718 | 0.721 | 0.716 |

PERSONALIZED TARGET SELECTION METHOD FOR NON-INVASIVE NEUROMODULATION TECHNOLOGY

CROSS-REFERENCE TO THE RELATED APPLICATIONS

This application is a continuation application of International Application No. PCT/CN2024/079519, filed on Mar. 1, 2024, which is based upon and claims priority to Chinese Patent Application No. 202310279372.1, filed on Mar. 21, 2023, the entire contents of which are incorporated herein by reference.

TECHNICAL FIELD

The present disclosure relates to the technical field of brain magnetic resonance imaging (MRI), and in particular to a personalized target selection method for a non-invasive neuromodulation technology.

BACKGROUND

Non-invasive neuromodulation is a biomedical engineering technology that utilizes physical (optical, magnetic, electrical, ultrasonic) signals to non-invasively alter the function of the nervous system. Neuromodulation (brain stimulation) is a physical therapy that alleviates mental symptoms by modulating the electric or magnetic fields in specific brain regions. Compared with invasive deep brain stimulation, non-invasive neuromodulation has the advantages of slight side effects and significant therapeutic effects. Typical non-invasive neuromodulation technologies, such as repetitive transcranial magnetic stimulation (rTMS) and transcranial direct current stimulation (tDCS), modulate brain neuron activity by stimulating specific brain regions, thereby alleviating symptoms of major mental diseases such as depression.

As a non-invasive imaging technique, magnetic resonance imaging (MRI) can help study brain function and diseases by monitoring brain activity and structure. Functional magnetic resonance imaging (fMRI) can identify brain regions associated with specific tasks by monitoring changes in blood oxygenation levels. Structural magnetic resonance imaging (sMRI) can provide information on brain structure, including gray matter, white matter, and ventricles. T1 data is an image format used to describe sMRI scan results, which can display the distribution and density of brain tissue and is commonly used to establish three-dimensional (3D) brain models.

Among the non-invasive neuromodulation technologies, fMRI and sMRI can help determine the stimulation location for non-invasive neuromodulation. fMRI can detect changes in brain activity so as to determine the location to stimulate the brain region. sMRI can provide information on brain structure to help determine the distance between the stimulation location and key brain regions and avoid interference with important brain regions. T1 data can be used to establish personalized brain models to help determine the stimulation location and intensity, thereby enabling more accurate stimulation therapy. Currently, when used to treat patients with depression, non-invasive neuromodulation typically employs fixed therapeutic targets. The therapeutic targets include: dorsolateral prefrontal cortex (DLPFC), dorsomedial prefrontal cortex (DMPFC), ventrolateral prefrontal cortex (VLPFC), and ventromedial prefrontal cortex (VMPFC), which can achieve successful modulation of emotional responses in some patients.

However, the effective rate of the above targets in actual treatment is only between 10% and 60%, and different patients may have different reactions to the same treatment method. Therefore, further research is needed to gain a deeper understanding of and determine the optimal personalized treatment method and target selection.

SUMMARY

(I) Technical Problem to Be Solved

In view of the above drawbacks in the prior art, the present disclosure provides a personalized brain region target selection method for a non-invasive neuromodulation technology.

(II) Technical Solution

To achieve the above objective, the present disclosure adopts the following technical solutions:

In a first aspect, an embodiment of the present disclosure provides a personalized target selection method for a non-invasive neuromodulation technology, including:

S10: preprocessing functional magnetic resonance imaging (fMRI) data from MRI scan data of a current patient to acquire preprocessed fMRI brain image feature data;

S20: inputting the preprocessed fMRI brain image feature data into a pre-trained inter-subtype classification model to acquire a subtype label of the current patient and all feature voxels of the subtype label;

S30: preprocessing T1-weighted MRI data of structural magnetic resonance imaging (sMRI) data from the MRI scan data of the current patient (preprocessing the sMRI data from the MRI scan data of the current patient) to acquire a skull outline; and registering the sMRI and fMRI data to acquire a transformation matrix T; and S40: performing, based on the transformation matrix T, coordinate transformation on all the feature voxels of the subtype label; calculating a distance between each voxel b on the skull outline and each feature voxel after coordinate transformation; marking a feature voxel with a distance less than a specified length as a response feature voxel of b; counting a number of response feature voxels corresponding to each voxel on the skull outline; and selecting a voxel with a largest number of response feature voxels on the skull outline as a candidate target for a corresponding personalized target;

where, the inter-subtype classification model is acquired by training a given classification model based on MRI scan data of a preset number of patients.

Optionally, before the step S20, the method further includes:

S001: preprocessing fMRI brain image data of a specified number of patients acquired in advance to acquire brain image features from the fMRI data of each patient;

S002: performing dimensionality reduction on each brain image feature to acquire low-dimensional image feature data; clustering, by a clustering algorithm, all the low-dimensional image feature data to acquire k subtypes; and marking each patient with a subtype label; and S003: taking the low-dimensional image feature data with the subtype label as first training data, and training the classification model to acquire the trained inter-subtype classification model.

Optionally, the brain image feature of the fMRI data includes but is not limited to following multidimensional features: amplitude of low frequency fluctuations (ALFF), regional homogeneity (ReHo), functional connectivity (FC), time series analysis of signal (including signal change amplitude and frequency distribution), spatial distribution feature (activity level of a specific brain region and connection strength of brain regions), frequency domain feature (energy or power spectral density of a specific frequency band), statistical indicator (mean, standard deviation, skewness, kurtosis of signals), graph theory indicator (centrality of nodes, modularity of networks, and clustering coefficient), and advanced features automatically extracted by a deep learning model;

the performing dimensionality reduction on each brain image feature to acquire low-dimensional image feature data is implemented by a dimensionality reduction algorithm algorithm including but not limited to:

t-distributed stochastic neighbor embedding (t-SNE), principal component analysis (PCA), unified manifold approximation and projection (UMAP), linear discriminant analysis (LDA), kernel PCA, self-organizing map (SOM), Gaussian random projection, and autoencoders; and the classification model includes but is not limited to following algorithms: support vector machine (SVM), convolutional neural network (CNN), decision trees, random forests, gradient boosting machines (GBM), K-nearest neighbors (KNN), logistic regression, multilayer perceptrons (MLP), recurrent neural networks (RNN), long short-term memory (LSTM), gated recurrent units (GRU), and self-attention mechanisms, etc.

Optionally, before the step S30, the method further includes:

selecting, for a single subtype, brain image feature data of all patients with a corresponding subtype label; acquiring fMRI data of a certain number of healthy individuals; acquiring, by a patient data preprocessing method, brain image feature data of the healthy individuals; training a binary classification machine learning (ML) model with a classification label of ill or not; identifying, by a recursive feature elimination (RFE) algorithm, corresponding feature voxels of the subtype; and recording the identified feature voxels in SList.

Optionally, the step S30 includes:

segmenting, by an MRI brain image skull segmentation algorithm, the T1-weighted MRI data to acquire the skull outline; and registering, by a brain image analysis method, the sMRI and fMRI data of the current patient to acquire the transformation matrix T;

where, the fMRI data is partial data of the MRI data of the current patient.

Optionally, the method further includes: performing, based on the transformation matrix T, coordinate transformation on each voxel in SList to acquire a feature voxel list $SList^T$ of the T1-weighted MRI data in a same coordinate system;

calculating, by a traversal method, a distance between each voxel b on the skull outline and each feature voxel $a^T$ in $SList^T$; marking, if the distance between b and $a^T$ is less than D, $a^T$ as a response voxel of b; and counting a number of response voxels of the voxel b; and sorting the number of response voxels of the voxel on the skull outline of the patient, and selecting a voxel with a largest number of response feature voxels on the skull outline within D as a candidate therapeutic target.

Optionally, in the step S10, the fMRI data of the current patient is preprocessed to acquire the preprocessed brain image feature data by:

preprocessing the fMRI data of the current patient; selecting a low frequency signal with a frequency between 0.01 Hz and 0.08 Hz; and calculating, by an ALFF calculation method, an ALFF value according to Eq. (1):

$$ALFF_i = \frac{\sum_{i=N_1}^{N_2} Y_i}{N_2 - N_1} \quad (1)$$

where, $ALFF_i$ denotes the ALFF value of a voxel, specifically a three-dimensional (3D) spatial coordinate point i of the brain image feature data; $Y_i$ denotes frequency domain data acquired by performing Fourier transform on time domain data of the voxel i; and $N_1$ and $N_2$ denote data index positions of a discrete frequency spectrum corresponding to selected lowest and highest frequencies, respectively; and finally, dividing the ALFF value of each voxel by an all-brain mean ALFF value to acquire a standardized ALFF result, and taking the standardized ALFF result as the preprocessed brain image feature data.

In a second aspect, an embodiment of the present disclosure further provides a computing device, including a memory and a processor, where the memory is configured to store a computer program; and the processor is configured to execute the computer program in the memory, thereby implementing the steps of the personalized target selection method for a non-invasive neuromodulation technology according to any one of the above paragraphs in the first aspect.

In a third aspect, a computer-readable storage medium is configured to store a computer program, where the computer program is executed by a processor to implement the steps of the personalized target selection method for a non-invasive neuromodulation technology according to any one of the above paragraphs in the first aspect.

(III) Beneficial Effects

The therapeutic target selection method of this embodiment combines brain MRI technology and a ML algorithm to classify the mental disease, automatically identifying suitable potential targets for rTMS for each subtype. The method selects the optimal therapeutic target by analyzing the patient's brain image data, reducing human subjective intervention on the treatment image and improving the objectivity and accuracy of treatment. The therapeutic target selection method provided by the present disclosure has a very broad application prospect, bringing new hope for the treatment of mental patients.

DETAILED DESCRIPTION OF THE EMBODIMENTS

To facilitate a better understanding of the present disclosure, the present disclosure is described in detail below with reference to the accompanying drawings and specific implementations.

In the clinical practice of the prior art, doctors are often based on their experience and preferences to choose a fixed single therapeutic target such as DLPFC for all patients. However, mental diseases such as depression are typical complex diseases with strong heterogeneity, and often with symptoms and causes varying greatly. Meanwhile, the human brain is a highly complex system, and specific targets can only image specific neural networks, ignoring other neural networks that may be related to diseases. Therefore, selecting only one specific therapeutic target cannot effectively treat all patients, and it is necessary to develop personalized target selection and treatment solutions for different patients with different conditions.

In order to solve the target selection problem of the non-invasive neuromodulation technology, the present disclosure proposes a new solution, that is, a personalized target selection method based on a brain MRI technology. Unlike traditional target selection methods, this method is a personalized target selection method based on big data analysis. It can identify the most suitable target locations for different patients' specific situations, thereby providing reasonable assistance for the treatment of mental diseases. Specifically, in this method, based on brain MRI data, differences between connections of different brain regions of the patient and those of a healthy control population are analyzed, and a specific brain region of patient is identified as a candidate for the personalized target. Compared with traditional target selection methods, the personalized target selection method of the present disclosure improves the accuracy and precision of target selection, promotes subsequent modulation effects, and has high clinical application value.

The non-invasive neuromodulation target selection method proposed in the embodiments of the present disclosure is based on brain MRI data and a ML method to achieve disease classification. The present disclosure can automatically identify suitable potential targets of rTMS for different subtypes of diseases. The method of the present disclosure eliminates the subjective interference of traditional treatment methods and provides a more objective and accurate solution for the treatment of mental diseases.

Embodiment 1

Figure 1:
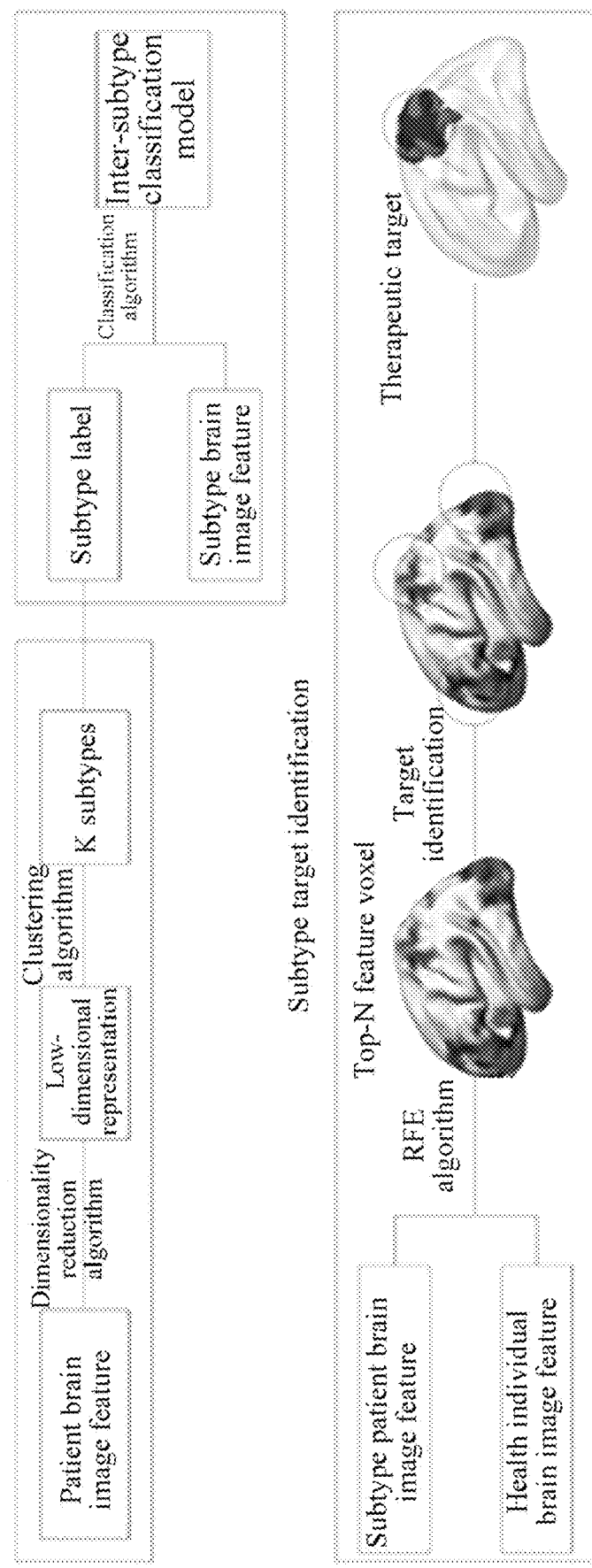
FIGS. 1 and 5 are flowcharts of a personalized target selection method for a non-invasive neuromodulation technology according to an embodiment of the present disclosure provides, including.
Figure 5:
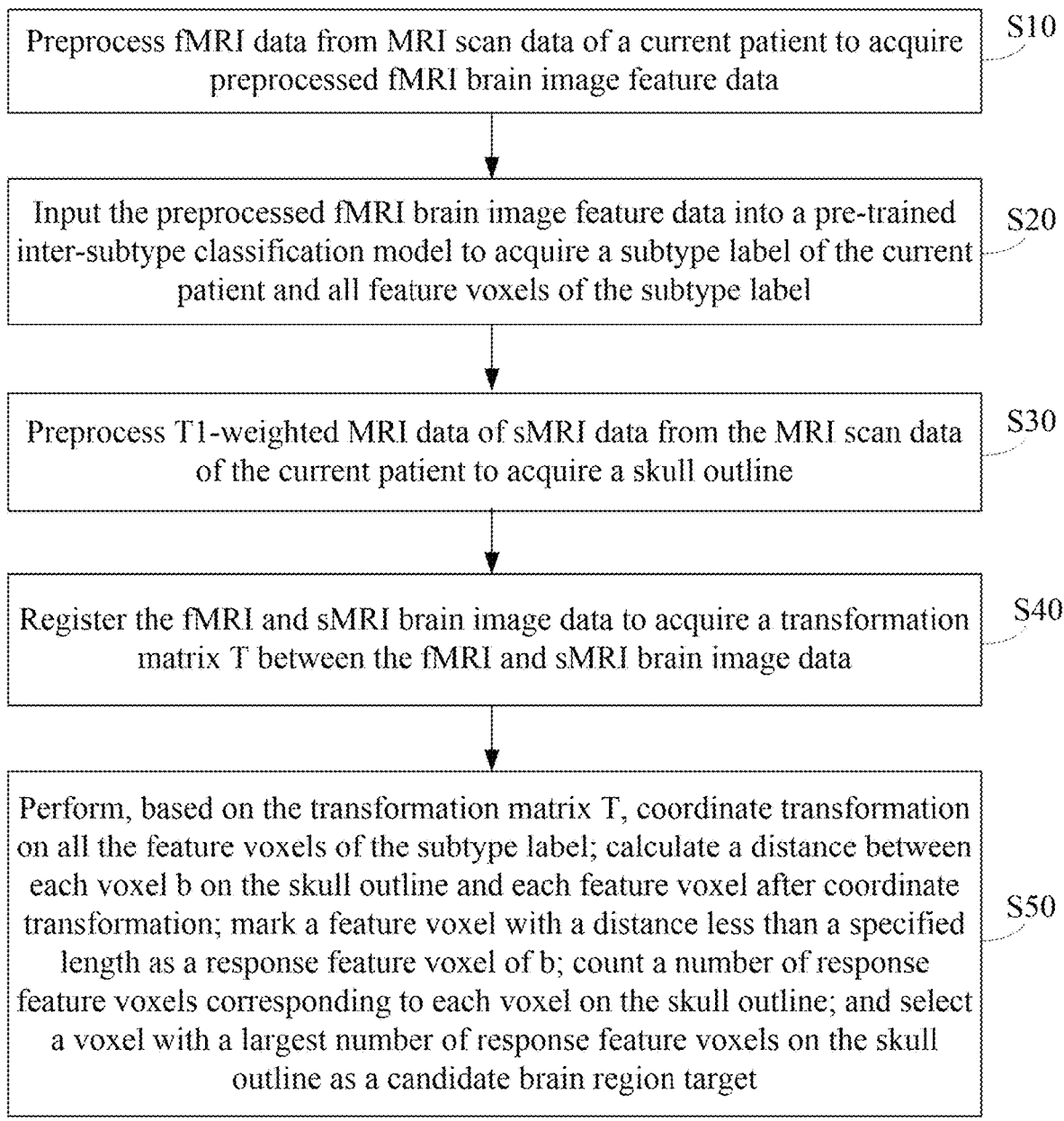

FIGS. 1 and 5 are flowcharts of a personalized target selection method for a non-invasive neuromodulation technology according to an embodiment of the present disclosure. In this embodiment, an executing subject of the method is any computing device. Specifically, the method includes the following steps.

S10. Functional magnetic resonance imaging (fMRI) data from MRI scan data of a current patient is preprocessed to acquire preprocessed fMRI brain image feature data.

In this embodiment, the MRI data of the patient includes fMRI—functional data, sMRI—structural data, etc., and sMRI includes weighted data such as T1 and T2.

S20. The preprocessed fMRI brain image feature data is input into a pre-trained inter-subtype classification model to acquire a subtype label of the current patient and all feature voxels of the subtype label.

That is to say, based on the MRI brain image of a specified patient, the patient's fMRI data is classified by the inter-subtype classification model to acquire the patient's subtype and corresponding subtype feature voxels.

S30. T1-weighted MRI data of structural magnetic resonance imaging (sMRI) data from the MRI scan data of the current patient is preprocessed to acquire a skull outline.

That is to say, the T1-weighted MRI data of the specified patient is segmented by a general MRI brain image skull segmentation algorithm to identify the skull outline in the specified patient's brain image.

S40. The sMRI and fMRI brain image data are registered to acquire transformation matrix T between the sMRI and fMRI brain image data.

S50. Based on the transformation matrix T, coordinate transformation is performed on all the feature voxels of the subtype label, and a distance between each voxel b on the skull outline and each feature voxel after coordinate transformation is calculated. A feature voxel with a distance less than a specified length is marked as a response feature voxel of b. A number of response feature voxels corresponding to each voxel on the skull outline is counted, and a voxel with a largest number of response feature voxels on the skull outline is selected as a candidate target for a corresponding personalized target.

That is to say, coordinate transformation is performed on each feature voxel of the patient's subtype to acquire feature voxel list $SList^T$ of T1 in the same coordinate system. The feature voxels, i.e. SList, belongs to the subtype. The individual patient is classified by the inter-subtype classification model to acquire the subtype label of the patient, thereby acquiring the feature voxels corresponding to the subtype, that is, SList.

A distance between each voxel b on the skull outline and each feature voxel $a^T$ in $SList^T$ is calculated by a traversal method. If the distance between b and $a^T$ is less than D, $a^T$ is marked as a response voxel of b, and a number of response voxels of the voxel b is counted.

The number of response voxels of the voxel on the skull outline of the patient is counted, and a voxel with a largest number of response feature voxels on the skull outline within D is selected as a candidate therapeutic target.

In this embodiment, the coordinate transformation of SList is to transform SList to the data space of T1, namely the space where the skull outline is located. $SList^T$ acquired by the transformation is located in the same space as the voxels on the skull outline, allowing for distance calculation.

In this embodiment, the inter-subtype classification model is acquired by training a given classification model based on the MRI data of a preset number of patients. For example, the MRI data of a specified number of patients acquired in advance are preprocessed to acquire each patient's fMRI data and brain image features of the fMRI data. Dimensionality reduction is performed on each brain image feature to acquire low-dimensional image feature data. All low-dimensional image feature data are clustered by a clustering algorithm to acquire k subtypes, and each patient is marked with a subtype label. Low-dimensional image feature data with a subtype label are taken as first training data, and the classification model is trained to acquire the trained inter-subtype classification model.

In this embodiment, a disease population subcategory (hereinafter referred to as subtype) classification model for mental disease population is provided. The acquisition of the model mainly includes two steps, namely subtype clustering and classification model training.

In the subtype clustering step, a combination of a dimensionality reduction algorithm and a clustering algorithm is used to acquire the subtype of the mental disease. Specifically, the fMRI data of the patient population is processed. Firstly, the dimensionality reduction algorithm is used to reduce the fMRI data to a specified dimension, while retaining important information. Then, the clustering algorithm is used to cluster the dimensionality-reduced data to acquire the subtype of the mental disease.

In the training step of the inter-subtype classification model, the inter-subtype classification model is trained based on the clustering subtype label acquired in the above step and the fMRI data of the patient. The established classification model is configured to predict the subtype of the patient.

In addition, for each subtype, the differences in the fMRI data of the patient population and the healthy population are identified for subsequent therapeutic target calculation. Firstly, the fMRI data of the healthy population are introduced. For each subtype, the values of the 3D spatial coordinate points (hereinafter referred to as voxels) of the fMRI data from patients and healthy individuals are used as features. The features are combined with the classification model, and the most important voxels in the classification process are identified as feature voxels through a RFE method.

Embodiment 2

This embodiment provides a more specific personalized target selection method for a non-invasive neuromodulation technology. This method is implemented in three stages, and the steps of each stage are described in detail below. The executing subject of the method in this embodiment is any computing device.

In a first stage, a subtype classification model for mental disease subtype classification is acquired based on brain MRI.

Step 11. Brain MRI data, or MRI data, of a specified number of individuals are acquired in advance, and fMRI data of the MRI data are preprocessed.

The MRI data can be retrieved from a hospital database or are image data acquired during a certain period of time. The MRI data may include: MRI data of a first preset number of patients with a specific type of disease, and resting-state fMRI brain image data of a second preset number of healthy individuals.

In this embodiment, the fMRI data of each individual is individually preprocessed. The preprocessing includes: removal of data from first 10 time points, head movement correction, registering to a standard brain space, smoothing, etc. In this embodiment, each preprocessing method is prior art, which is not limited in this embodiment but selected according to actual needs.

Step 12. Based on the preprocessed fMRI data of each individual, the brain image features of the fMRI data of each individual are acquired.

In this embodiment, the brain image features may include: ALFF, ReHo, FC, etc. This embodiment is not limited to these three features, and the features can be set according to actual needs.

Step 13. All patients' brain image features acquired in the step 12 are subjected to dimensionality reduction to acquire a low-dimensional brain image feature data of each brain image feature data in d-dimensional representation (d is much smaller than the original dimension of the brain image).

In this embodiment, dimensionality reduction algorithms such as t-SNE, PCA, and UMAP can be used for dimensionality reduction. Other dimensionality reduction algorithms can also be selected for dimensionality reduction, and this embodiment is not limited to the above algorithms. In this step, the d-dimensional representation can be selected according to actual needs, where d is a natural number greater than or equal to 2 and less than or equal to 5.

Step 14. The low-dimensional image feature data of all patients' fMRI data are clustered by the clustering algorithm to acquire k subgroups of the disease population. In this embodiment, the subgroups of the disease population are referred to as subtypes. Each patient is assigned a subtype label, meaning that the low-dimensional image feature data of each patient's fMRI data corresponds to a subtype label.

In this embodiment, the clustering algorithm may include Gaussian mixture model (GMM), k-means clustering, spectral clustering, etc.

Step 15. Based on the low-dimensional image feature data of all patients' fMRI data in the step 13 and the subtype labels in the step 14, a given classification model is trained to acquire the inter-subtype classification model.

In this embodiment, methods such as five-fold cross-validation and parameter grid search are used during the training process to ensure the training effect of the classification model. The classification algorithm can be SVM or CNN, etc.

The processing object of the steps 13, 14, and 15 are data of a certain number of patients, excluding data of healthy individuals.

In a second stage, candidate feature voxels of different subtypes of the mental disease are screened.

Step 16. The image feature data of the fMRI data of healthy individuals with a similar number of patients with a first subtype label are acquired.

It is understandable that the image feature data of the fMRI data of the healthy individuals are acquired through the method used in the step 12.

Step 17. A diseased label is assigned to the image feature data of the patient with the first subtype label, and a non-diseased label is assigned to the image feature data of the healthy individual.

A binary classification ML model (such as SVM and random forests) is trained based on the image feature data with a diseased label and that with a non-diseased label. Based on the trained binary classification ML model, the most important voxels (3D spatial coordinate points of the MRI data) in the classification process are identified as feature voxels through a RFE method, and the acquired feature voxels are recorded in SList.

The processing object here is the 3D image feature data (such as ALFF and ReHo) in the step 12, so there are voxels or 3D spatial coordinate points.

In a third stage, personalized targets are screened.

Step 18. A general MRI brain image skull segmentation algorithm is used to segment the brain image of the T1-weighted MRI data of the sMRI data of the specified analyzed patient, thereby identifying the skull outline in the patient's brain image.

The MRI data includes fMRI—functional image data and sMRI—structural image data.

Step 19. The sMRI data and the fMRI data of the specified analyzed patient are aligned through general brain image analysis software such as SPM12's coregister module to acquire the transformation matrix T.

Step 20. Coordinate transformation is performed on each feature voxel in the subtype of the specified analyzed patient. That is, for any feature voxel a in SList, the following transformation is performed: $a^T = a*T$, thereby acquiring the feature voxel list $SList^T$ with the T1 coordinate.

After the patient data are classified, the subtype label of the patient is acquired, thereby acquiring the SList corresponding to the subtype.

Step 21. Each voxel b on the skull outline of the specified analyzed patient is tranversed, and the distance between b and each feature voxel $a^T$ in $Slist^T$ is calculated. If the distance between b and $a^T$ is less than D, $a^T$ is marked as the response voxel of b, and the number of response voxels of the voxel b is counted.

Step 22. The number of response voxels on the skull outline of the specified analyzed patient is sorted. A voxel with a largest number of response feature voxels within D on the skull outline is selected as a candidate therapeutic target.

The method of this embodiment combines brain MRI technology and a ML algorithm to classify the mental disease, automatically identifying suitable potential targets for rTMS for each subtype. The method selects the optimal therapeutic target by analyzing the patient's brain image data, reducing human subjective intervention on the treatment image and improving the objectivity and accuracy of treatment. The therapeutic target selection method provided by the present disclosure has a very broad application prospect, bringing new hope for the treatment of mental patients.

Embodiment 3

This embodiment provides a more specific personalized target selection method for a non-invasive neuromodulation technology. This method is implemented in three stages, and the steps of each stage are described in detail below. The executing subject of the method in this embodiment is any computing device.

Step 031. Brain MRI scans are performed on all patients with severe depression and healthy individuals by an MRI scanner of GE Signa HDxt 3.0T.

This experiment acquires data from 372 patients with severe depression and 254 healthy individuals, and functional images are acquired through gradient echo planar imaging (EPI) sequences.

The parameters include: repetition time (TR)=500 ms, echo time (TE)=30 ms, flip angle=60°, field of view=224× 224 mm², and matrix=64×64. 35 axial slices with a thickness of 3.5 mm and a gap of 0.5 mm are acquired. Participants are required to close their eyes to rest, but remain awake during the scanning process.

Step 032. The fMRI data of the patients and healthy individuals are preprocessed using data processing assistant for resting-state fMRI (DPABI) of the digital analysis and computation software Matlab. The preprocessing methods include: removing of the data from the first 10 scanning time points, adjustment of the order of layer scanning, head motion correction, adjustment of the scanning order, registering to standard Montreal space, and smoothing to improve signal-to-noise ratio, reduce registration inaccuracy, and remove linear drift, etc.

Step 033. Based on the preprocessed data in the step 032, the brain image features of the patients and healthy individuals, such as ALFF data, are continuously calculated.

According to the ALFF calculation method, a low frequency signal with frequencies between 0.01 Hz and 0.08 Hz is selected to calculate the ALFF value, as shown in Eq. (1) below:

$$ALFF_i = \frac{\sum_{i=N_1}^{N_2} Y_i}{N_2 - N_1} \quad (1)$$

where, $ALFF_i$ denotes the ALFF value of a voxel, specifically a 3D spatial coordinate point i of the brain image feature data; $Y_i$ denotes frequency domain data acquired by performing Fourier transform on time domain data of the voxel i; and $N_1$ and $N_2$ denote data index positions of a discrete frequency spectrum corresponding to selected lowest and highest frequencies, respectively. Finally, the ALFF value of each voxel is divided by an all-brain mean ALFF value to acquire a standardized ALFF result.

In a first stage, the inter-subtype classification model for mental disorders is acquired based on brain MRI.

The inter-subtype classification model is configured to classify the fMRI data of specific patients, identify the corresponding subtype (disease population subcategory) of the patient, and then identify the personalized therapeutic target for non-invasive neuromodulation.

Step 034. The dimensionality of the ALFF data of all patients is reduced to 2 dimensions by a t-SNE algorithm.

The specific parameter settings for the dimensionality reduction algorithm are as follows. The complexity parameter related to the number of nearest neighbors in the model is set to 30, the learning rate of the model is set to 200, the maximum number of iterations of the model is set to 1,000, and the distance evaluation standard of the model is Euclidean distance.

Step 035. The 2D data of the patients acquired through dimensionality reduction in the step 034 are clustered by a GMM clustering algorithm to acquire 2 subtypes, and each patient is assigned a subtype label.

Figures 2, 3:
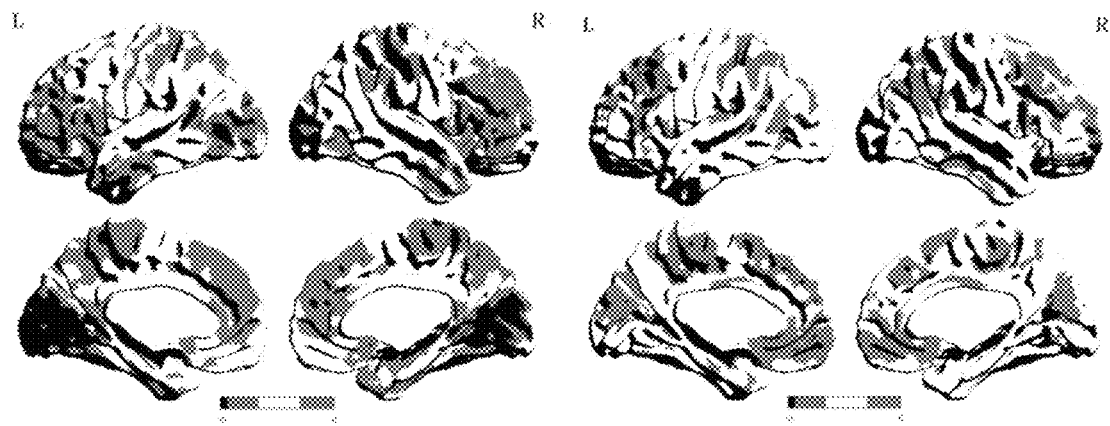
FIG. 2 is a brain image feature diagram of a t-test for a subtype and a healthy individual according to an embodiment of the present disclosure.
FIG. 3 is a classification performance diagram of top-50 voxels and all-brain voxels according to an embodiment of the present disclosure.

The specific parameter settings for the clustering algorithm are as follows. A generalized covariance matrix is set for each subtype in the model. When the lower limit average gain is below the threshold of 0.001, the model iteration is stopped. The maximum number of iterations is set to 100, and the weight and mean of the model are initialized by a k-means algorithm. Two subtypes are named as 0 and 1, respectively. Based on the ALFF data of the subtypes and healthy individuals, a two-sample t-test is conducted, and the brain imaging results are shown in FIG. 2.

Step 036. Based on the 2D data of all patients acquired in the step 034 and the corresponding subtypes of the patients acquired in the step 035 and used as classification labels, the data are divided in a ratio of 8:2. That is, 80% of the data forms a training set, and the remaining 20% of the data forms a testing set. Based on the training set, a SVM classification algorithm is used to acquire optimal model parameters through a combination of grid search and 5-fold cross validation. The search model parameters include kernel functions (linear, nonlinear) and kernel coefficients (0.01, 0.03, 0.05). Then based on the testing set, the performance of the inter-subtype classification model is tested, and ultimately the inter-subtype classification model is acquired.

Step 037. A certain number of healthy individuals are selected based on a specific subtype of patients. Based on the ALFF data of subtype patients and healthy individuals, as well as the classification labels of ill or not, the data are divided according to the ratio of 8:2. That is, 80% of the data forms the training set, and the remaining 20% of the data forms the testing set.

Firstly, based on the training set, a RFE algorithm is used to identify the top-50 voxels with the highest classification contribution among the subtypes and healthy individuals as feature voxels. RFE is a popular feature selection algorithm that recursively reduces the voxel set based on the importance of each voxel, ultimately leaving important core voxels. The following are the detailed steps of RFE.

1) Initialization. All voxels of ALFF form an initial voxel set, and the number of feature voxels to be selected is set to 50.
2) Voxel weight calculation. A SVM classifier is trained based on the training set data, and the weight score of each voxel is calculated. The SVM classifier separates the data of the specific subtypes of patients and healthy individuals based on the training set data, and the weight score of each voxel is calculated based on the contribution of the voxel in the classification.
3) Voxel sorting. The voxels are sorted in descending order of weight score.
4) Voxel removal. Voxels with the lowest weight score are removed from the voxel set, and this process is repeated until only a preset number of voxels remain.
5) Model training and evaluation. The SVM classifier is retrained based on residual voxels, and model performance is evaluated based on the testing set data. Cross-validation and other techniques are used to evaluate the generalization ability of the model.
6) Termination condition. If a required number of voxels are acquired, the algorithm terminates. Otherwise, the processing returns to the step 2) to continue iterating.

The above algorithms are all from the scikit-learn software package.

Secondly, based on the testing set, the top-50 feature voxels identified are combined with the labels of the subtypes and healthy individuals to train the same linear SVM classification model as described above. The classification performance is tested based on the testing set and compared with the performance of the model trained using all the voxel features. From the results, the top-50 feature voxels approach or exceed the classification performance of voxels in all brain voxel regions. This indicates the potential of the top-50 feature voxels as biomarkers and as therapeutic targets. The specific results are shown in FIG. 3.

The above process is to search for the feature voxels of each subtype, which can be used for subsequent target calculations.

In a second stage, personalized therapeutic targets of patients are screened.

Step 038. MRI scans are performed on specific patients and scan data are acquired.

Step 039. The fMRI data from the MRI scans of the patients are preprocessed to acquire ALFF data. T1-weighted MRI data from the sMRI data of the patients are preprocessed by FreeSurfer software, including denoising, correction, and other steps.

Step 040. Based on the preprocessed T1-weighted MRI data, skull segmentation is performed on the T1-weighted MRI data by a skullstrip module of FreeSurfer software to acquire a skull outline, and a voxel list on the skull outline is recorded as OVList.

Step 041. General brain image analysis software, such as the CoreRegister module of SPM12, is used to perform an image alignment task in an automatic or semi-automatic mode. This module uses normalized mutual information as a similarity measure for image registration. In the method of the present disclosure, sMRI data and fMRI data are registered through this module to acquire the transformation matrix T.

Step 042. The same method in the step 034 is used to reduce the dimensionality of the patient's ALFF data so as to acquire 2D data. Based on the inter-subtype classification model acquired in the step 037, the 2D data is classified to acquire the patient's subtype label and the corresponding feature voxel list SList for the subtype.

Step 043. Coordinate transformation is performed on each feature voxel of the patient's subtype. That is, for any voxel a in SList, the transformation $a^T = a*T$ is performed to acquire the feature voxel list $SList^T$ with the T1 coordinate.

Step 044. All voxels of OVLists on the skull outline of the patient acquired in the step 040 are traversed, and the distance between each voxel b on the skull outline and each feature voxel $a^T$ in $Slist^T$. When the distance between b and $a^T$ is less than D, $a^T$ is recorded as the response voxel of b, and the number of response voxels of the voxel b is counted.

Figure 4:
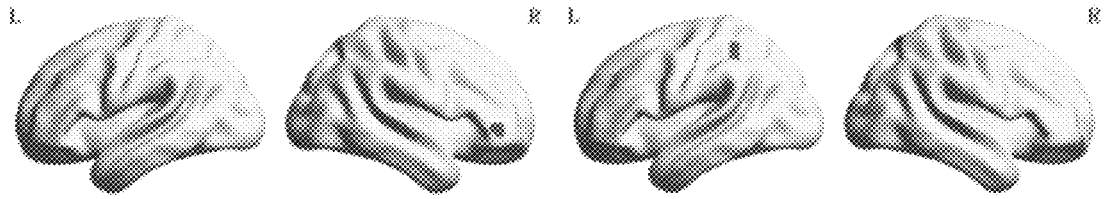
FIG. 4 is a subtype target diagram according to an embodiment of the present disclosure.

Step 045. The number of response voxels on the skull outline of the patient is sorted. The voxels on the skull outline with a largest number of response feature voxels within the distance range D serve as the candidate therapeutic targets, as shown in FIG. 4.

The method combines brain MRI technology and a ML algorithm to classify the mental disease, automatically identifying suitable potential targets for rTMS for each subtype. The method selects the optimal therapeutic target by analyzing the patient's brain image data, reducing human subjective intervention on the treatment image and improving the objectivity and accuracy of treatment. The therapeutic target selection method provided by the present disclosure has a very broad application prospect, bringing new hope for the treatment of mental patients.

In another aspect, an embodiment of the present disclosure further provide a computer-readable storage medium. The computer-readable storage medium is configured to store a computer program, where the computer program is executed by a processor to implement the steps of the personalized brain region target selection method for a non-invasive neuromodulation technology according to any one of the above embodiments.

It should be noted that, in the claims, any reference signs placed between parentheses shall not be construed as limiting the claim. The word "include" does not exclude the presence of components or steps not listed in the claims. The word "a/an" or "one" preceding an element does not exclude the existence of multiple such components. The present disclosure can be implemented with the assistance of hardware including several different components and the assistance of a properly programmed computer. In the claims where several apparatuses are listed, several of the apparatuses may be embodied by the same hardware item. The words first, second, third, etc. are used for convenience of expression only and do not imply any order. These words can be understood as part of the component name.

In addition, it should be noted that in the description of this specification, the description with reference to the terms such as "one embodiment", "some embodiments", "embodiment", "example", "specific example" or "some examples" means that specific features, structures, materials or characteristics described in connection with the embodiment or example are included in at least one embodiment or example of the present disclosure. In this specification, the schematic expression of the above terms is not necessarily directed to the same embodiment or example. Moreover, the specific features, structures, materials, or characteristics described may be combined in a suitable manner in any one or more embodiments or examples. In addition, those skilled in the art may combine different embodiments or examples described in this specification and characteristics of the different embodiments or examples without mutual contradiction.

Although preferred embodiments of the present disclosure have been described, those skilled in the art can make additional alterations and modifications to these embodiments once they learn the basic inventive concept. Therefore, the appended claims are intended to be interpreted as including the preferred embodiments and all alterations and modifications falling within the scope of the present disclosure.

Obviously, those skilled in the art can make various alterations and modifications to the present disclosure without departing from the spirit and scope of the present disclosure. The present disclosure is intended to cover these modifications and variations provided that they fall within the scope of protection defined by the following claims and their equivalent technologies.

The invention claimed is:

1. A personalized target selection method for a noninvasive neuromodulation technology, comprising:
S10: preprocessing functional magnetic resonance imaging (fMRI) data from MRI scan data of a current patient to acquire preprocessed fMRI brain image feature data;
S20: inputting the preprocessed fMRI brain image feature data into a pre-trained inter-subtype classification model to acquire a subtype label of the current patient and all feature voxels of the subtype label;
S30: preprocessing T1-weighted MRI data of structural magnetic resonance imaging (sMRI) data from the MRI scan data of the current patient to acquire a skull outline; and registering the sMRI and fMRI data to acquire a transformation matrix T; and
S40: performing, based on the transformation matrix T, coordinate transformation on all the feature voxels of the subtype label; calculating a distance between each voxel b on the skull outline and each feature voxel after coordinate transformation; marking a feature voxel with a distance less than a predetermined length as a response feature voxel of b; counting a number of response feature voxels corresponding to each voxel on the skull outline; and selecting a voxel with a largest number of response feature voxels on the skull outline as a candidate target for a corresponding personalized target;
wherein the pre-trained inter-subtype classification model is acquired by training a given classification model based on MRI scan data of a preset number of patients.

2. The personalized target selection method according to claim 1, wherein before the step S20, the personalized target selection method further comprises:
S001: preprocessing fMRI brain image data of a predetermined number of patients acquired in advance to acquire brain image features from the fMRI data of each patient;
S002: performing dimensionality reduction on each brain image feature to acquire low-dimensional image feature data; clustering, by a clustering algorithm, all the low-dimensional image feature data to acquire k subtypes; and marking each patient with a subtype label; and
S003: taking the low-dimensional image feature data with the subtype label as first training data, and training a classification model to acquire a trained inter-subtype classification model.

3. The personalized target selection method according to claim 2, wherein
the brain image feature of the fMRI data comprises: amplitude of low frequency fluctuations (ALFF), regional homogeneity (ReHo), or functional connectivity (FC);
the step of performing the dimensionality reduction on each brain image feature to acquire the low-dimensional image feature data comprises:
performing, by t-distributed stochastic neighbor embedding (t-SNE), principal component analysis (PCA), or unified manifold approximation and projection (UMAP), the dimensionality reduction on each brain image feature to acquire the low-dimensional image feature data; and
the classification model is support vector machine (SVM), or convolutional neural network (CNN).

4. The personalized target selection method according to claim 2, wherein before the step S30, the personalized target selection method further comprises:
selecting, for a single subtype, brain image feature data of all patients with a corresponding subtype label; acquiring fMRI data of a predetermined number of healthy individuals; acquiring, by a patient data preprocessing method, brain image feature data of the healthy individuals; training a binary classification machine learning (ML) model with a classification label of ill or not; identifying, by a recursive feature elimination (RFE) algorithm, corresponding feature voxels of the subtype; and recording identified feature voxels in SList.

5. The personalized target selection method according to claim 4, wherein the step S30 comprises:
segmenting, by an MRI brain image skull segmentation algorithm, the T1-weighted MRI data to acquire the skull outline; and
registering, by a brain image analysis method, the sMRI and fMRI data of the current patient to acquire the transformation matrix T;
wherein the fMRI data is partial data of the MRI scan data of the current patient.

6. The personalized target selection method according to claim 5, wherein the personalized target selection method further comprises:
performing, based on the transformation matrix T, coordinate transformation on each voxel in SList to acquire a feature voxel list $SList^T$ of the T1-weighted MRI data in a same coordinate system;
calculating, by a traversal method, a distance between each voxel b on the skull outline and each feature voxel $a^T$ in $SList^T$; marking, when the distance between b and $a^T$ is less than D, $a^T$ as a response voxel of b; and counting a number of response voxels of the voxel b; and
sorting the number of response voxels of the voxel on the skull outline of the patient, and selecting a voxel with a largest number of response feature voxels on the skull outline within D as a candidate therapeutic target.

7. The personalized target selection method according to claim 5, wherein in the step S10, the fMRI data of the current patient is preprocessed to acquire preprocessed brain image feature data by:

preprocessing the fMRI data of the current patient; selecting a low frequency signal with a frequency between 0.01 Hz and 0.08 Hz; and calculating, by an ALFF calculation method, an ALFF value according to Eq. (1):

$$ALFF_i = \frac{\sum_{i=N_1}^{N_2} Y_i}{N_2 - N_1} \quad (1)$$

wherein $ALFF_i$ denotes the ALFF value of a voxel, comprising a three-dimensional (3D) spatial coordinate point i of the brain image feature data; $Y_i$ denotes frequency domain data acquired by performing Fourier transform on time domain data of the voxel i; and $N_1$ and $N_2$ denote data index positions of a discrete frequency spectrum corresponding to selected lowest and highest frequencies, respectively; and dividing the ALFF value of each voxel by an all-brain mean ALFF value to acquire a standardized ALFF result, and taking the standardized ALFF result as the preprocessed brain image feature data.

8. A computing device, comprising a memory and a processor, wherein the memory is configured to store a computer program; and the processor is configured to execute the computer program in the memory to implement the steps of the personalized target selection method for the non-invasive neuromodulation technology according to claim 1.

9. A non-transitory computer-readable storage medium, configured to store a computer program, wherein the computer program is executed by a processor to implement the steps of the personalized target selection method for the non-invasive neuromodulation technology according to claim 1.

10. The computing device according to claim 8, wherein before the step S20 of the personalized target selection method, the personalized target selection method further comprises:

S001: preprocessing fMRI brain image data of a predetermined number of patients acquired in advance to acquire brain image features from the fMRI data of each patient;

S002: performing dimensionality reduction on each brain image feature to acquire low-dimensional image feature data; clustering, by a clustering algorithm, all the low-dimensional image feature data to acquire k subtypes; and marking each patient with a subtype label; and S003: taking the low-dimensional image feature data with the subtype label as first training data, and training a classification model to acquire a trained inter-subtype classification model.

11. The computing device according to claim 10, wherein in the personalized target selection method, the brain image feature of the fMRI data comprises: amplitude of low frequency fluctuations (ALFF), regional homogeneity (ReHo), or functional connectivity (FC);

the step of performing the dimensionality reduction on each brain image feature to acquire the low-dimensional image feature data comprises:

performing, by t-distributed stochastic neighbor embedding (t-SNE), principal component analysis (PCA), or unified manifold approximation and projection (UMAP), the dimensionality reduction on each brain image feature to acquire the low-dimensional image feature data; and the classification model is support vector machine (SVM), or convolutional neural network (CNN).

12. The computing device according to claim 10, wherein before the step S30 of the personalized target selection method, the personalized target selection method further comprises:

selecting, for a single subtype, brain image feature data of all patients with a corresponding subtype label; acquiring fMRI data of a predetermined number of healthy individuals; acquiring, by a patient data preprocessing method, brain image feature data of the healthy individuals; training a binary classification machine learning (ML) model with a classification label of ill or not; identifying, by a recursive feature elimination (RFE) algorithm, corresponding feature voxels of the subtype; and recording identified feature voxels in SList.

13. The computing device according to claim 12, wherein the step S30 of the personalized target selection method comprises:

segmenting, by an MRI brain image skull segmentation algorithm, the T1-weighted MRI data to acquire the skull outline; and registering, by a brain image analysis method, the sMRI and fMRI data of the current patient to acquire the transformation matrix T;

wherein the fMRI data is partial data of the MRI scan data of the current patient.

14. The computing device according to claim 13, wherein the personalized target selection method further comprises:

performing, based on the transformation matrix T, coordinate transformation on each voxel in SList to acquire a feature voxel list $SList^T$ of the T1-weighted MRI data in a same coordinate system;

calculating, by a traversal method, a distance between each voxel b on the skull outline and each feature voxel $a^T$ in $SList^T$; marking, when the distance between b and $a^T$ is less than D, $a^T$ as a response voxel of b; and counting a number of response voxels of the voxel b; and sorting the number of response voxels of the voxel on the skull outline of the patient, and selecting a voxel with a largest number of response feature voxels on the skull outline within D as a candidate therapeutic target.

15. The computing device according to claim 13, wherein in the step S10 of the personalized target selection method, the fMRI data of the current patient is preprocessed to acquire preprocessed brain image feature data by:

preprocessing the fMRI data of the current patient; selecting a low frequency signal with a frequency between 0.01 Hz and 0.08 Hz; and calculating, by an ALFF calculation method, an ALFF value according to Eq. (1):

$$ALFF_i = \frac{\sum_{i=N_1}^{N_2} Y_i}{N_2 - N_1} \quad (1)$$

wherein $ALFF_i$ denotes the ALFF value of a voxel, comprising a three-dimensional (3D) spatial coordinate point i of the brain image feature data; $Y_i$ denotes frequency domain data acquired by performing Fourier transform on time domain data of the voxel i; and $N_1$ and $N_2$ denote data index positions of a discrete frequency spectrum corresponding to selected lowest and highest frequencies, respectively; and dividing the ALFF value of each voxel by an all-brain mean ALFF value to acquire a standardized ALFF result, and taking the standardized ALFF result as the preprocessed brain image feature data.

16. The non-transitory computer-readable storage medium according to claim 9, wherein before the step S20 of the personalized target selection method, the personalized target selection method further comprises:

S001: preprocessing fMRI brain image data of a predetermined number of patients acquired in advance to acquire brain image features from the fMRI data of each patient;

S002: performing dimensionality reduction on each brain image feature to acquire low-dimensional image feature data; clustering, by a clustering algorithm, all the low-dimensional image feature data to acquire k subtypes; and marking each patient with a subtype label; and S003: taking the low-dimensional image feature data with the subtype label as first training data, and training a classification model to acquire a trained inter-subtype classification model.

17. The non-transitory computer-readable storage medium according to claim 16, wherein in the personalized target selection method, the brain image feature of the fMRI data comprises: amplitude of low frequency fluctuations (ALFF), regional homogeneity (ReHo), or functional connectivity (FC);

the step of performing the dimensionality reduction on each brain image feature to acquire the low-dimensional image feature data comprises:

performing, by t-distributed stochastic neighbor embedding (t-SNE), principal component analysis (PCA), or unified manifold approximation and projection (UMAP), the dimensionality reduction on each brain image feature to acquire the low-dimensional image feature data; and the classification model is support vector machine (SVM), or convolutional neural network (CNN).

18. The non-transitory computer-readable storage medium according to claim 16, wherein before the step S30 of the personalized target selection method, the personalized target selection method further comprises:

selecting, for a single subtype, brain image feature data of all patients with a corresponding subtype label; acquiring fMRI data of a predetermined number of healthy individuals; acquiring, by a patient data preprocessing method, brain image feature data of the healthy individuals; training a binary classification machine learning (ML) model with a classification label of ill or not; identifying, by a recursive feature elimination (RFE) algorithm, corresponding feature voxels of the subtype; and recording identified feature voxels in SList.

19. The non-transitory computer-readable storage medium according to claim 18, wherein the step S30 of the personalized target selection method comprises:

segmenting, by an MRI brain image skull segmentation algorithm, the T1-weighted MRI data to acquire the skull outline; and registering, by a brain image analysis method, the sMRI and fMRI data of the current patient to acquire the transformation matrix T;

wherein the fMRI data is partial data of the MRI scan data of the current patient.

20. The non-transitory computer-readable storage medium according to claim 19, wherein the personalized target selection method further comprises:

performing, based on the transformation matrix T, coordinate transformation on each voxel in SList to acquire a feature voxel list $SList^T$ of the T1-weighted MRI data in a same coordinate system;

calculating, by a traversal method, a distance between each voxel b on the skull outline and each feature voxel $a^T$ in $SList^T$; marking, when the distance between b and $a^T$ is less than D, $a^T$ as a response voxel of b; and counting a number of response voxels of the voxel b; and sorting the number of response voxels of the voxel on the skull outline of the patient, and selecting a voxel with a largest number of response feature voxels on the skull outline within D as a candidate therapeutic target.

* * * * *